(12) United States Patent
Berenfeld et al.

(10) Patent No.: US 11,564,607 B2
(45) Date of Patent: Jan. 31, 2023

(54) METHOD AND SYSTEM FOR MAPPING AND ANALYZING CARDIAC ELECTRICAL ACTIVITY

(71) Applicant: THE REGENTS OF THE UNIVERSITY OF MICHIGAN, Ann Arbor, MI (US)

(72) Inventors: Omer Berenfeld, Ann Arbor, MI (US); Hakan Oral, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1521 days.

(21) Appl. No.: 15/092,335

(22) Filed: Apr. 6, 2016

(65) Prior Publication Data

US 2016/0317093 A1    Nov. 3, 2016

Related U.S. Application Data

(60) Provisional application No. 62/155,286, filed on Apr. 30, 2015.

(51) Int. Cl.
*A61B 5/287* (2021.01)
*A61B 5/00* (2006.01)
(Continued)

(52) U.S. Cl.
CPC .............. *A61B 5/287* (2021.01); *A61B 5/068* (2013.01); *A61B 5/361* (2021.01); *A61B 5/6858* (2013.01);
(Continued)

(58) Field of Classification Search
CPC ..... A61B 5/0422; A61B 5/046; A61B 5/6858; A61B 5/068; A61B 5/7253;
(Continued)

(56) References Cited

U.S. PATENT DOCUMENTS 5,662,108 A     9/1997  Budd et al.
6,016,437 A  *  1/2000  Tu ........................ A61B 5/0422
                                                        600/374
(Continued)

FOREIGN PATENT DOCUMENTS

EP          2259740 A2      12/2010
WO       WO-199406349 A1     3/1994
WO       WO-2009105720 A2    8/2009

OTHER PUBLICATIONS

International Preliminary Report on Patentability from International Application No. PCT/US2016/026230 dated Oct. 31, 2017.
(Continued)

*Primary Examiner* — Eun Hwa Kim
*Assistant Examiner* — Catherine C. Premraj
(74) *Attorney, Agent, or Firm* — Marshall, Gerstein & Borun LLP (57) ABSTRACT

A multiple-point basket-type or crown-shaped catheter device provides simultaneously mapping over a three-dimensional (3D) region of a subject, such as, one or more chambers of a subject's heart. The catheter device may include a series of splines each having a wave-like profile formed of a periodic series of peaks and troughs, with electrodes located at the peaks and troughs for mapping purposes.

19 Claims, 5 Drawing Sheets

(51) Int. Cl.
  *A61B 18/14* (2006.01)
  *A61B 5/06* (2006.01)
  *A61B 5/361* (2021.01)
  *A61B 34/20* (2016.01)
  *A61B 18/00* (2006.01)
  *A61B 17/00* (2006.01)

(52) U.S. Cl.
  CPC ........ *A61B 5/7253* (2013.01); *A61B 18/1492* (2013.01); *A61B 34/20* (2016.02); *A61B 2017/00044* (2013.01); *A61B 2017/00048* (2013.01); *A61B 2017/00053* (2013.01); *A61B 2018/0016* (2013.01); *A61B 2018/00267* (2013.01); *A61B 2018/00351* (2013.01); *A61B 2018/00839* (2013.01); *A61B 2018/00892* (2013.01); *A61B 2018/00898* (2013.01); *A61B 2562/04* (2013.01)

(58) Field of Classification Search
  CPC ............ A61B 2562/04; A61B 18/1492; A61B 2018/00267; A61B 5/287; A61B 5/361; A61B 2018/0016; A61B 2018/00351; A61B 2018/00839; A61B 2018/00892; A61B 2018/00898; A61B 34/20; A61B 2017/00044; A61B 2017/00048; A61B 2017/00053
  See application file for complete search history.

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,826,420 B1 | 11/2004 | Beatty et al. |
| 6,826,421 B1 | 11/2004 | Beatty et al. |
| 6,978,168 B2 | 12/2005 | Beatty et al. |
| 6,990,370 B1 | 1/2006 | Beatty et al. |
| 7,289,843 B2 | 10/2007 | Beatty et al. |
| 8,208,998 B2 | 6/2012 | Beatty et al. |
| 2003/0176799 A1 | 9/2003 | Beatty et al. |
| 2005/0101874 A1 | 5/2005 | Beatty et al. |
| 2006/0052716 A1 | 3/2006 | Beatty et al. |
| 2006/0058588 A1* | 3/2006 | Zdeblick ................ A61N 1/368 600/300 |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2007/0083194 A1* | 4/2007 | Kunis ................ A61B 18/1492 606/41 |
| 2009/0209950 A1 | 8/2009 | Starksen |
| 2010/0094274 A1* | 4/2010 | Narayan .............. A61B 5/0402 606/33 |
| 2010/0204560 A1* | 8/2010 | Salahieh ............ A61B 18/1492 600/373 |
| 2012/0271138 A1* | 10/2012 | Kordis ............... A61B 18/1492 600/375 |
| 2013/0006238 A1* | 1/2013 | Ditter ................... A61B 5/0422 606/41 |
| 2015/0223757 A1* | 8/2015 | Werneth ............... A61B 5/0422 600/301 |
| 2016/0000450 A1* | 1/2016 | Yu ......................... B23K 26/40 606/159 |

OTHER PUBLICATIONS

Berenfeld, et al. "Frequency-Dependent Breakdown of Wave Propagation Into Fibrillatory Conduction Across the Pectinate Muscle Network in the Isolated Sheep Right Atrium," Circ.Res. 90:1173-1180 (2002).
Berenfeld, et al. "Spatially distributed dominant excitation frequencies reveal hidden organization in atrial fibrillation in the Langendorff-perfused sheep heart," J.Cardiovasc.Electrophysiol. 11:869-879 (2000).
Davidenko, et al. "Stationary and drifting spiral waves of excitation in isolated cardiac muscle," Nature 355: 349-351 (1992).
Gray, et al. "Spatial and temporal organization during cardiac fibrillation," Nature 392:75-78 (1998).
Haissaguerre, et al., "Driver Domains in Persistent Atrial Fibrillation," Circulation 130:530-538 (2014).
Jalife, et al. "Mechanisms of atrial fibrillation: mother rotors or multiple daughter wavelets, or both?," J Cardiovasc Electrophysiol 9:S2-12 (1998).
Mansour, et al. "Left-to-Right Gradient of Atrial Frequencies During Acute Atrial Fibrillation in the Isolated Sheep Heart," Circulation 103:2631-2636 (2001).
Narayan, "Conventional ablation for atrial fibrillation with or without focal impulse and rotor modulation (the CONFIRM trial)," Abstract, Heart Rhythm Society Scientific Sessions (2011).
Rabinovitch et al., "Singular Value Decomposition of Optically-Mapped Cardiac Rotors and Fibrillatory Activity," Journal of Physics D: Applied Physics, 48(9):095401, 10 pages (2015).
Rodrigo, et al., "Body surface localization of left and right atrial high-frequency rotors in atrial fibrillation patients: Aclinical-computational study," Heart Rhythm 11(9):1584-1591 (2014).
Warren, et al. "IK1 blockade reduces frequency, increases organization and terminates ventricular fibrillation in the guinea pig heart," PACE 24:647-647 (2001).
International Search Report and Written Opinion from PCT/US2016/026230 dated Jul. 28, 2016.

\* cited by examiner

METHOD AND SYSTEM FOR MAPPING AND ANALYZING CARDIAC ELECTRICAL ACTIVITY

CROSS-REFERENCE TO RELATED APPLICATION

This application claims the benefit of U.S. Application Ser. No. 62/155,286, filed Apr. 30, 2015, entitled "Method and System for Mapping and Analyzing Cardiac Electrical Activity," which is hereby incorporated by reference in its entirety.

STATEMENT OF GOVERNMENT SUPPORT

This invention was made with government support under grant numbers HL039707 and HL118304 awarded by the National Institutes of Health. The government has certain rights in this invention.

FIELD OF THE INVENTION

The present disclosure relates generally to identifying cardiac electrical activity in a subject and, more particularly, to mapping and analyzing cardiac electrical activity using a multipoint sensing catheter.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Cardiac arrhythmias are caused by misfiring of electrical impulses that coordinate cardiac myocytes to effectively pump blood. Electrophysiology studies are used to elucidate the mechanism of activation and resulting impulse propagation through cardiac tissue to identify specific patterns of sequential depolarization. This has enabled the recognition of macro-reentrant or micro-reentrant, automatic, and triggered patterns, and characterized the contribution of depolarizations in arrhythmias.

Researchers have developed technologies designed for the detection of electrical signals on the endocardial and epicardial surfaces of the heart, where cardiac mapping is used to anatomically localize and time cardiac depolarization.

Nonetheless, complex cardiac arrhythmias, such as atrial fibrillation (AF), atrial tachycardia (AT), and sustained ventricular tachycardia (VT) and ventricular fibrillation (VF) still present significant treatment challenges, especially given that anti-arrhythmic medications do not effectively control all the symptoms associated with these rhythm disorders.

AF, for example, is a chronic progressive disease that is caused by a complex interaction between initiating triggers and an abnormal substrate capable of sustaining the arrhythmia that may become permanent with time. AF causes electrical and structural remodeling of the atria, which in turn contribute to the persistence of AF.

Paroxysmal AF is commonly treated with ablation that isolates pulmonary veins, but success rates of pulmonary veins isolation in patients with persistent AF is limited as electrical isolation of pulmonary vein foci is frequently insufficient. Additional linear ablation and/or ablation targeting complex fractionated atrial electrograms (CFAEs) are often used, which frequently result in the destruction of vast and possibly unnecessary portions of the right and left atrium.

Intracardiac mapping has been used to guide catheter ablation procedures and position the ablation catheter within the heart chamber. Such intracardiac mapping creates 3D activation maps within the cardiac anatomy to identify the sources of abnormal rhythm targeted for ablation, and to reduce the reliance on fluoroscopy which is a radiation hazard for both patients and physicians.

The two most widely used electroanatomic mapping systems utilize contact-based catheter localization technology that is magnetic-based or impedance-based. Non-contact based mapping systems use balloon catheters with multi-electrode arrays. Non-contact technology allows analysis of the activation in non-sustained, polymorphic, or hemodynamically intolerant tachycardia.

Despite their existence, these mapping techniques are still deficient. The present techniques simply are incapable of (i) identifying patterns of electrical activity, and by virtue of that, (ii) identifying points for potential ablation, with sufficient desired accuracy. Better identification and analysis of cardiac electrical activity is desired.

SUMMARY OF THE INVENTION

Techniques are provided to map and analyze cardiac electrical activity through the use of a multiple point basket type catheter capable of simultaneously mapping a three dimensional (3D) region of a subject, specifically one or more chambers of the heart.

In accordance with an example, a catheter comprising: an housing providing a sheath to an extendable catheter within the housing; and the extendible catheter comprising a plurality of splines extendable within the housing when the catheter is in a non-deployed state, the plurality of splines collectively extending through an opening in the housing and into a deployed state where the splines erect into a generally three dimensional (3D) shaped catheter head, wherein each of the plurality of splines comprises non-conducting regions, and wherein each of the plurality of splines further comprises electrodes distributed across the respective spline to collect electrical activity signal data across the spline, such that in the deployed state the catheter comprises electrodes positioned for collecting electrical activity signal data over a volumetric space within a target chamber.

In accordance with an example, an electrical activity mapping system comprising: a catheter comprising: an housing providing a sheath to an extendable catheter within the housing; and the extendible catheter comprising a plurality of splines extendable within the housing when the catheter is in a non-deployed state, the plurality of splines collectively extending through an opening in the housing and into a deployed state where the splines erect into a generally three dimensional (3D) shaped catheter head, wherein each of the plurality of splines comprises non-conducting regions, and wherein each of the plurality of splines further comprises electrodes distributed across the respective spline to collect electrical activity signal data across the spline, such that in the deployed state the catheter comprises electrodes positioned for collecting electrical activity signal data over a volumetric space within a target chamber; one or more processors coupled to the electrodes of the catheter; and one or more non-transitory computer readable memories coupled to the one or more processors, wherein the one or more memories include computer-executable instructions stored therein that, when executed by the one or more processors, cause the one or more processors to: receive electrical signal data from at least some of the plurality of electrodes of the catheter; map electrical activity within a chamber from the electrical signal data; identify, from the mapping, (i) potential sources of fibrillation and/or arrhythmia within the chamber and/or (ii) an alarm condition indicating the presence or onset of fibrillation and/or arrhythmia.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Figure 1A:
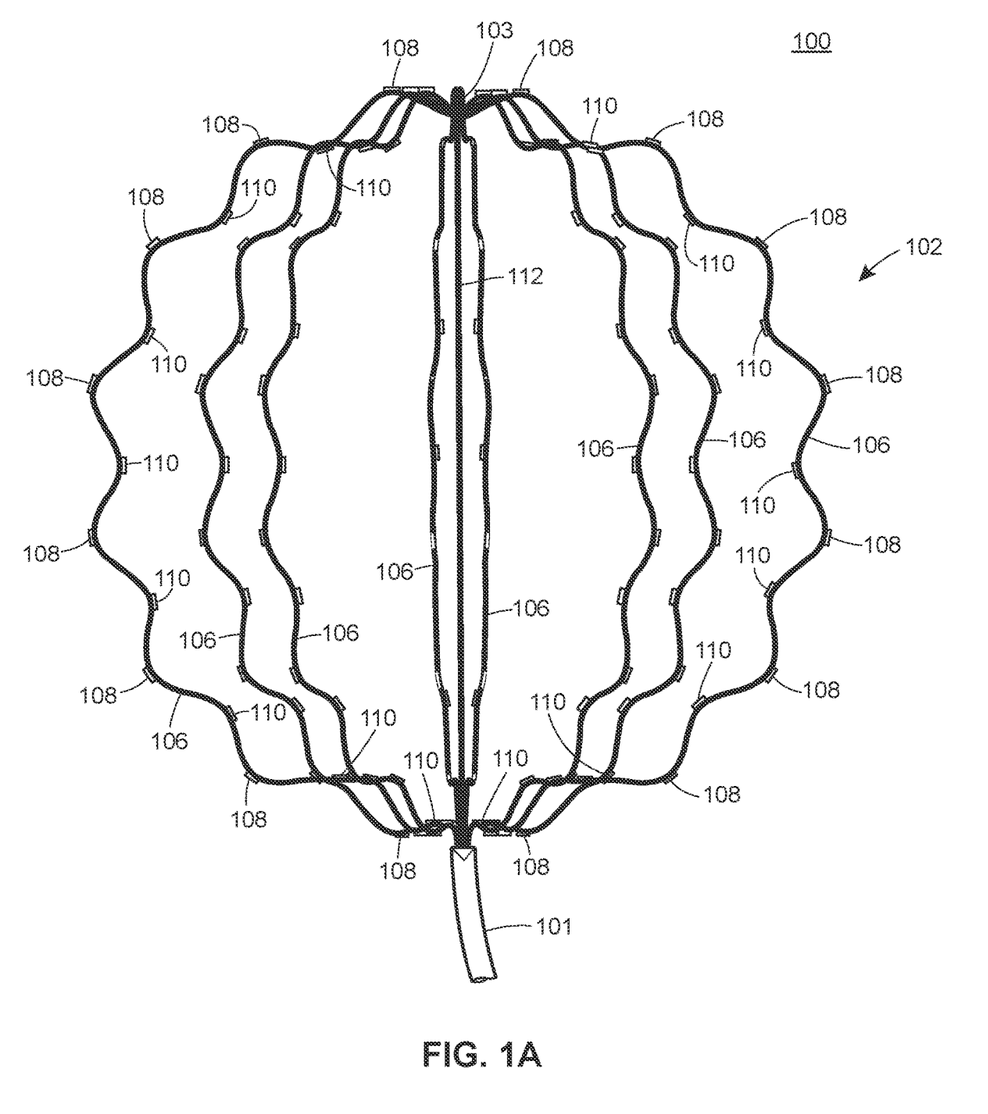
FIG. 1A illustrates a multiple electrode catheter having a plurality of exterior electrodes and a plurality of interior electrodes, in accordance with an example catheter configuration.

FIG. 1A illustrates a catheter 100 in accordance with an example. Generally speaking, the catheter 100 has a basket-type, or crown, catheter configuration. The configuration is by way of example, as the particular implementation of the catheter 100 may be vary in different examples. The catheter 100 includes a deployment sleeve or housing 101 within which a deployable head 102 may be sheathed in an insertion stage of the catheter deployment. The housing 101 may be formed of a suitable biologically inert material, as would be used by a catheter housing. Example materials included, silicones, polyvinyl chloride (PVC), plastics, or other suitable flexible materials.

The deployable head 102 includes a plurality of an electrically isolating (non-conducting) members and a plurality of electrodes, each spaced apart, from other electrodes. The plurality of electrodes includes at least two different types of electrodes, which are positioned on a series of splines 106 (i.e., extending members) that define head 102. One set of the electrodes includes externally positioned electrodes 108. The other set of electrodes includes internally positioned electrodes 110. The indications of "external" and "internal" reflect a relative position of the sets of electrodes. The electrode may also be arranged such that the "external" 108 electrodes are facing only outward of the head 102 and the "internal" electrodes are facing inward on the head 102. In other examples, different sets of electrodes may be positioned otherwise. Moreover, while the electrodes are described as separated into two categories, the electrodes may be divided into greater numbers of sets. For example, the central wire 112 that serves to push/pull/steer the head 102 to change its shape and orientation relative to the housing shaft 101 may also be mounted with spaced electrodes along itself. In any event, the electrodes are positioned on or in the splines 106 and extend across the head 102, i.e., about the basket crown.

The illustrated example, the splines 106 are dual electrode splines. That is, each spline 106 contains multiple external electrodes 108 and multiple internal electrodes 110. In this way, because the catheter splines take on a basket configuration, the electrodes of the two different types may be geometrically positioned throughout the heart chamber, whether deployed in the atrium or ventricle.

In the deployed position, i.e., with the catheter head 102 erected into the basket-like shape, some portions of the splines 106 are in contact with the inner endocardial wall surface of the heart chamber or in close proximity to that wall surface. In particular, those portions of the wavy-curved splines 106 that contain outer electrodes are designed to contact the inner endocardial wall with greater efficacy than a straight-curved spline. In this position, the electrodes are able to acquire, analyze, and record electrical signals over a multidimensional region of interest on the endocardial wall.

In the deployed position, i.e., with the catheter head 102 erected into the basket-like shape, some portions of the splines 106 are not in contact with the inner endocardial wall surface of the heart chamber. In particular, those portions of the wavy-curved splines 106 that contain inner electrodes 110 are designed to avoid being in contact with the inner endocardial wall with greater efficacy than a straight-curved spline. In this position, the electrodes are able to acquire, analyze, and record electrical signals over a multidimensional region of interest within the heart cavity. Those signals may serve as voltage references, far-field sensors, or they may be used for delivery of currents as part of an active mapping approach.

In the example of FIG. 1A, the catheter head 102 includes 8 splines 106. Generally speaking, any number of splines can be used, e.g., 4 splines to 10 splines. The splines 106 extend along an arcuate path from an opening in the sheath 101 to a distal point 103 where the splines 106 meet. The splines 106 take on this arcuate shape, at least, when the head 102 is in the deployed position. The arcuate shape allows the splines 106 to approximately cover a spherical shape that positions electrodes over a three dimensional volume, thus forming a basket shape.

Figure 1B:
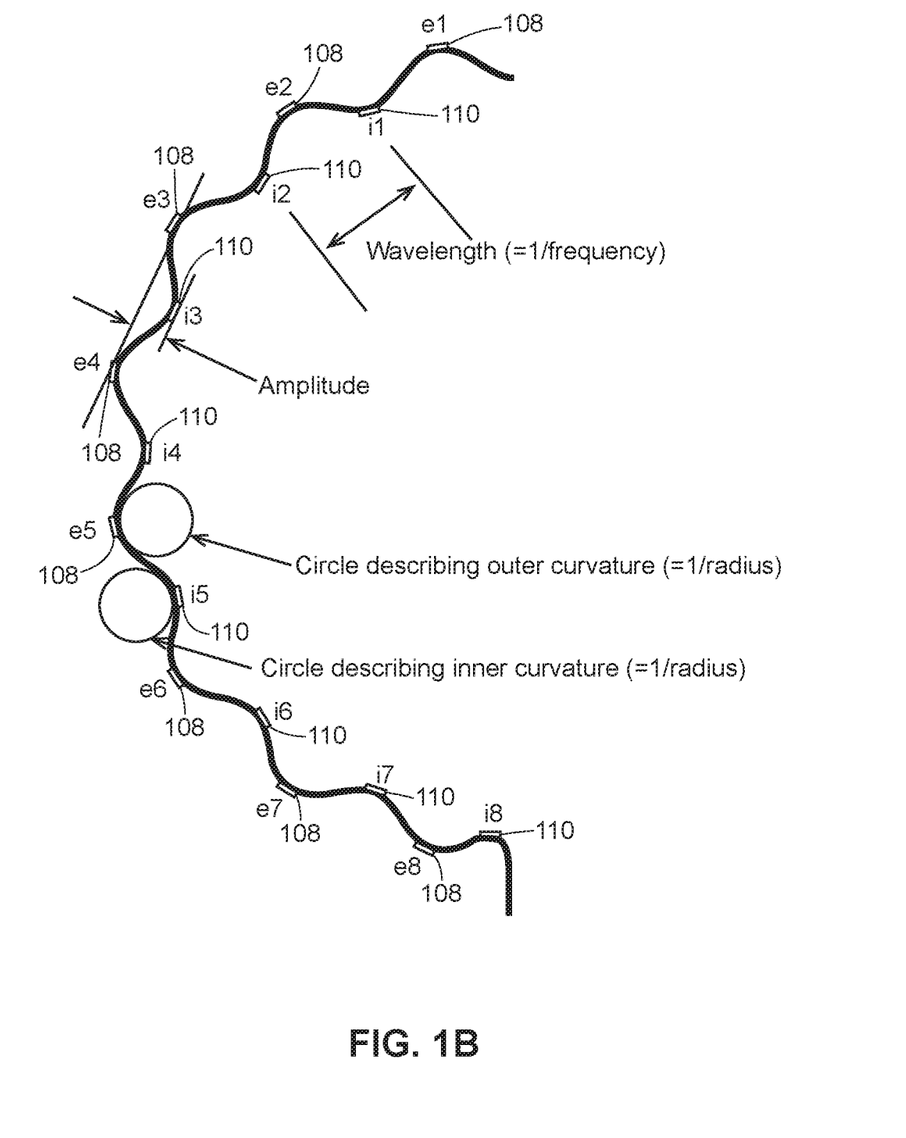
FIG. 1B illustrates a portion of one of the electrodes for the catheter of FIG. 1A.

In addition to the arcuate shape, each spline 106 has a wave-like profile, when viewed from the side, as shown in FIG. 1B which depicts one such spline 106. Each of the splines 106 includes a multitude of electrodes, e.g., between 4 to 16 electrodes. The wave-like profile provides the splines 106 a periodic series of peaks and troughs, where the repeating peaks provide locations for positioning the exterior electrodes 108 and the repeating troughs provide locations for positioning the interior electrodes 110. The wave like profile of the splines 106 improves the consistency of positioning of the electrodes against the walls of the heart chamber. Heart chambers sizes can vary greatly amongst subjects, in size and in geometry. The arcuate shape and wave-like profile allow the catheter head 102 to adapt to these different sizes and geometries. With this undulating profile, the overall head shape is not just that of a basket-like catheter, but further what is termed herein a "crown" shape. The crown shape is able to maintain contact between a heart chamber wall and certain electrodes, while preventing certain other electrodes from contacting that chamber wall. This simultaneous contact/non-contact state of the electrodes can be achieved independently from the position and angle of entrance of the catheter into the cardiac chamber because the central wire 112 is designed to bend distally from the exit of sleeve 101. The splines 106 are symmetrical about a central axis of the head 102, which further facilitates position independence.

The wave-like profile may be achieved two different ways: waves either in the plane of the spline, or waves perpendicular to the plane of the spline (i.e., in the plane of the sphere). For perpendicular plane orientations, the plurality of electrodes will not include both external and internal electrodes, but rather all electrodes would be external or surrounding the spline.

Each spline 106 has external electrodes 108 designed to contact the inner wall surface of the heart chamber and internal electrodes 110 designed to avoid contact with that inner wall. Through these electrodes, positioned on peaks and troughs, respectively, of the splines 106, mapping may be performed over the entire inner heart chamber simultaneously. This mapping enables a type of active mapping.

The splines 106 are characterized by a basket radius, measured from an arcuate centerline between the peaks and troughs to a center point. This basket radius is an approximate radius for the head 102 when in the deployed position, i.e., where the head 102 has the most circular shape. The splines 106 are also characterized by a wavelength value, which is measured peak-to-peak or trough-to-trough, as shown. The splines 106 are also characterized by a peak-to-trough wave amplitude, as well as by inner curvature circles and outer curvature circles. By adjusting any one or more of these variables, the geometry of the head 102 can be changed. For example, in some examples the inner curvature circle and the outer curvature circle have the same radius. In other examples, they have different radiuses. In some examples, the same inner curvature circles are used throughout the spline. In some examples, the same outer curvature circles are used throughout the spline. In some examples, the inner curvatures may vary throughout the spine; and in some examples the outer curvatures may vary throughout the spline. Further still, in some examples, instead of inner and outer curvature circles, other shapes may be used, such as half circles, half ellipses, etc. The geometry of the inner defining element may be the same or different than the outer defining element. The geometries may change throughout the spline. Further still, in addition to curvatures and shapes, the heights of the peaks and troughs throughout the spline may be fixed or vary. Any of these and other variations may be made to allow for any of a variety of waveforms on the spline. Further still, the number of electrodes within a group can be adjusted by adjusting the wavelength. The circumferential distances between the external and internal electrodes are also adjustable, by adjusting the wavelength of the wave-like profile as well as by adjusting the position of the electrodes on that profile.

A central wire 112 extends along the central axis of the catheter head 102. The central wire 112 may be a central push/pull/steer wire, attached to the distal apex 103 of the basket head 102. The central wire 112 is adjustable along the central axis to change the diameter of the catheter head (i.e., basket head) 102. The central wire 112 is adjustable to collapse and retract the basket head 102.

The central wire 112 may be formed of a sufficient enough rigidity to provide steering of the head 102 in different angular directions. That steering will enable adjustment of the shape and direction of the head 102 relative to the direction of the distal point of central axis. By changing the diameter (through push/pull movement) and shape (through steering) of the basket head 102 it will be possible to (i) conform to different volumes and shapes of the cardiac chamber independently of the angle of entrance and (ii) acquire different sets of data in the same cavity to develop/validate and improve interpolation algorithms.

In examples where the central wire 112 is steerable that provides geometrical control over the entire set of electrodes in the basket head 102, thereby allowing for more consistent contact between the external electrodes and the inner wall of the heart chamber. The pivoting point of this steering should be approximately in middle position of the central wire 112, between the exit of sleeve 101 and the distal apex 103 to enable motion of the distant part pole (distal apex 103 of the basket head 102) relative to the proximal pole location and to give more flexibility to the head 102 relative to angle of the entrance to the cardiac chamber, which is the angle of the sleeve 101.

Figure 2:
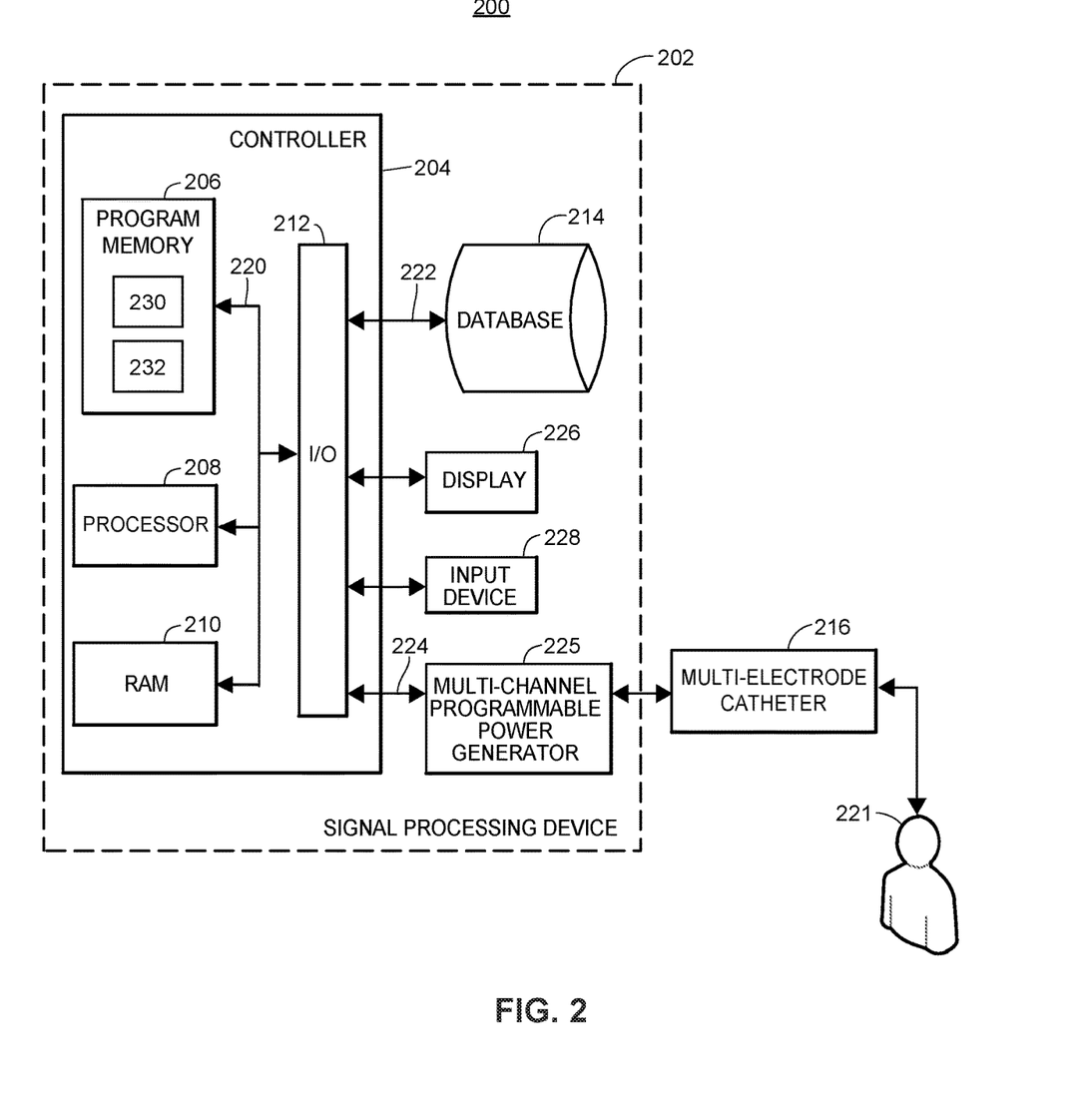
FIG. 2 is a schematic view of an apparatus for mapping and analyzing electrical cardiac activity using a multi-electrode catheter device, such that in FIG. 1.

The catheter 100 is coupled to a computer system that collects electrical signal data from the plurality of electrodes, and thus from many cardiac sites, simultaneously. FIG. 2 illustrates a computer system 200 for mapping and analyzing cardiac electrical activity. The computer system 200 specifically controls a multi-electrode catheter device 216, such as the catheter assembly 100, to map electrical activity in one or more chambers of the heart or in other vascular regions of the body, whether arterial or venous. The system 200 may be implemented in a desktop computer, laptop computer, tablet computer, mobile device smartphone, network-enabled health monitoring device, cloud based server, an application server, a web server, etc. The computer system 200 may represent a single one of these processing machines or a distributed combination of such processing machines.

A signal-processing device 202 (or "signal processor" or "diagnostic device") is coupled to a patient 221 through a multi-electrode catheter 216 (e.g., the catheter 100) in accordance with the teachings herein. The signal-processing device 202 may have a controller 204 operatively connected to a database 214 via a link 222 connected to an input/output (I/O) circuit 212. It should be noted that, while not shown, additional databases may be linked to the controller 204 in a known manner. The controller 204 includes a program memory 206, one or more processors 208 (may be called microcontrollers or a microprocessors), a random-access memory (RAM) 210, and the input/output (I/O) circuit 212, all of which are interconnected via an address/data bus 220. It should be appreciated that although only one processor 208 is shown, the controller 204 may include multiple microprocessors 208. Similarly, the memory of the controller 204 may include multiple RAMs 210 and multiple program memories 206. Although the I/O circuit 212 is shown as a single block, it should be appreciated that the I/O circuit 212 may include a number of different types of I/O circuits. The RAM(s) 210 and the program memories 206 may be implemented as semiconductor memories, magnetically readable memories, and/or optically readable memories, for example. A link 224, which may include one or more wired and/or wireless (Bluetooth, WLAN, etc.) connections, may operatively connect the controller 204 to catheter assembly 216 through the I/O circuit 212. In some examples, a multi-channel programmable power generator controller 225 is coupled to the catheter assembly 216, through the link 224, to provide current/voltage to the "active" electrodes in the catheter assembly 216. The catheter assembly 216 may include a multi-electrode catheter as described herein and that is inserted into the patient 221. In some examples, control aspects are embedded within that catheter assembly 216, as well. Reference number 216, therefore, may be used in reference to any number of these elements of the sensor assembly.

The program memory 206 and/or the RAM 210 may store various applications (i.e., machine readable instructions) for execution by the processor 208. For example, an operating system 230 may generally control the operation of the signal-processing device 202 and provide a user interface for the signal-processing device 202 to implement the configuration stages of the catheter 100 described herein. The program memory 206 and/or the RAM 210 may also store a variety of subroutines 232 for accessing specific functions of the signal-processing device 202. By way of example, and without limitation, the subroutines 232 may include, among other things: a subroutine for collecting electrical signal data from electrodes in the catheter 216, a subroutine for filtering the electrical signal data from the electrodes in the catheter 216, a subroutine generating a reference signal from the electrical data recorded in the catheter 216, a subroutine performing convolution between a stored or calculated reference signal, or signals, and the signals from the electrical data recorded in the catheter 216, a subroutine generating a unipolar signals or difference signals (e.g., bipolar signals) from the data originating at the electrical data recorded in the catheter 216, a subroutine performing singular value decomposition, or principal component analysis, and reconstruction on the electrical signal data, a subroutine for performing a frequency domain analysis to determine dominant frequencies and corresponding electrodes, a subroutine for performing a phase domain analysis to determine activation phase locations and corresponding electrodes, a subroutine to display the results of the other subroutines on a color-coded 2- or 3-dimensional spatial map, a subroutine to interpolate data points in discrete points onto a continuous 2- or 3-dimensional surface, a subroutine to present the recorded and processed signals in movie or video format, a subroutine to identify potential locations for fibrillation or arrhythmia in a chamber, and a subroutine to produce instructions for an ablation device to target these locations.

The subroutines 232 may include a subroutine to generate a health report and/or alarm condition, for example, using the display 226. That health report and/or alarm condition may be displayed as a web page, mobile device alert, tactile alert or alarm (e.g., via a vibrating function of a smartwatch or smartphone), or any other suitable visual and/or tactile (haptic) display. The subroutines 232 may communicate this health report and/or alarm condition to a separate computing device connected to the system 200 through a network connection. Such separate computing devices may include a server, laptop computer, handheld computer, health monitor, mobile device such as a cellular phone or Wi-Fi-enabled tablet, or other device. The subroutines 232 may include a subroutine to communicate the mapped electrical activity data or a health report, alarm condition, or other analysis thereof to a treatment system, such as therapeutic delivery system for administering a therapeutic treatment to a subject. The subroutines 232 may also include other subroutines, for example, implementing software keyboard functionality, interfacing with other hardware in the signal-processing device 202, etc. The subroutines 232 may also include other subroutines, for example, implementing software keyboard functionality, interfacing with other hardware in the signal-processing device 202, etc. The program memory 206 and/or the RAM 210 may further store data related to the configuration and/or operation of the signal-processing device 202, and/or related to the operation of the one or more subroutines 232. For example, the data may be data gathered by the sensor 216, data determined and/or calculated by the processor 208, etc. In addition to the controller 204, the signal-processing device 202 may include other hardware resources. The signal-processing device 202 may also include various types of input/output hardware such as a visual display 226 and input device(s) 228 (e.g., keypad, keyboard, etc.). In an embodiment, the display 226 is touch-sensitive, and may cooperate with a software keyboard routine as one of the software routines 232 to accept user input. It may be advantageous for the signal-processing device 202 to communicate with a broader medical treatment network (not shown) through any of a number of known networking devices and techniques (e.g., through a commuter network such as a hospital or clinic intranet, the Internet, etc.). For example, the apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

Although depicted as separate entities or components in FIG. 2, it is understood that any or all of the signal processing functionality and/or components of the signal-processing device 202 may be combined within an external electrical activity monitoring device, such as within an ECG monitoring machine. In this manner, the system 200 may both gather data about the patient 221 using a deployed catheter and process the gathered data to extract one or more features. In other examples, the activity monitoring device may be mobile device, such as a cellular or Wi-Fi phone, tablet, or other portable device. In some examples, the activity monitoring device may be a wearable device. In each such instance, the device may be connected to the catheter through a peripheral connector or wireless communication link, i.e., to a wireless controller of the catheter.

Separately, although depicted as a single component in FIG. 1, the catheter assembly 216 may include a plurality of the same type or different types of catheters. Moreover, the catheter assembly 216 may represent an endoscopic device including imagining functionality, ablation functionality, etc. and combinations thereof.

Figure 3:
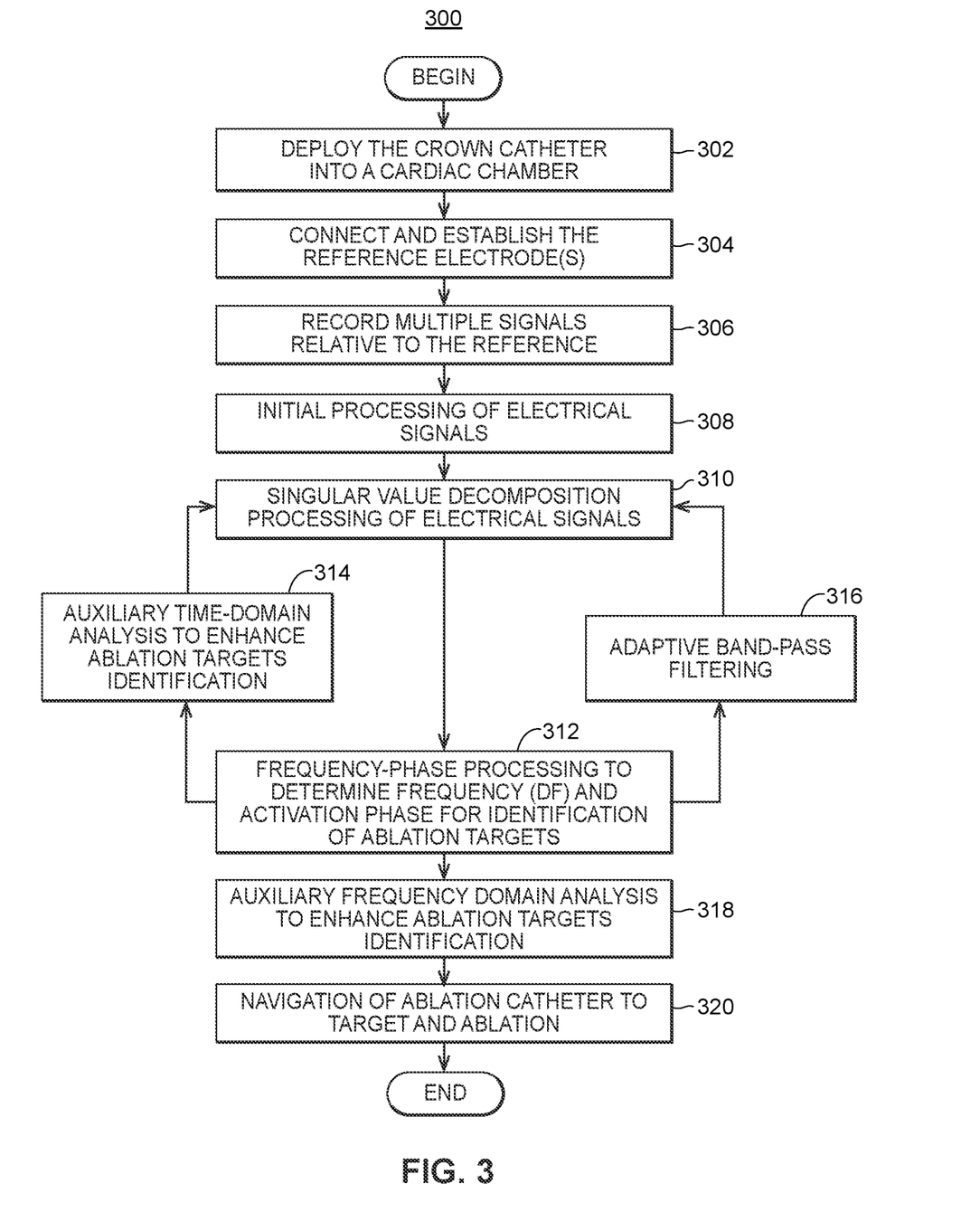
FIG. 3 is a flow diagram of an example implementation of a process for mapping and analyzing electrical cardiac activity to control ablation treatments in a subject.

FIG. 3 illustrates an example process 300 that includes, among other things, executing a computer-implemented method of mapping electrical activity mapping and analyzing that activity to determine targets for treatment, such as ablation. These executable instructions may be executed on the computer system 200, for example.

At a block 302, a multi-electrode, crown catheter is deployed in a cardiac chamber of a subject, where the catheter can be deployed into a basket shape, and activated for electrical operation. The catheter may also be mechanically adjusted and/or tilted to a desired shape and orientation within the cardiac chamber.

As part of the electrical operation, at a block 304, the computer system may establish a reference electrode (or signal path) to provide a baseline for the electrical signal data collected by catheter. For example, the computer system 200, executing the processing blocks of process 400, may operate the catheter 100 in a reference mode, in which a reference signal is supplied to the catheter 100 to establish one or more reference electrodes. The reference signal provides a baseline signal path from which the received electrical signals are compared. This allows the signals on the electrodes of the catheter 100 to be normalized, in effect, against the particular conditions of the subject, e.g., location of the catheter within the heart chamber or vascular region, differences in sizes of the chamber or region, orientation of the catheter in the chamber or region. For the crown-shaped catheter, the reference signal may also provide an orientation point about which the position of the other electrodes is determined by the control system.

The control system sends the reference signal on an electrical connection, either to the full set of electrodes on the catheter 100 or to a subset of the electrodes.

Using a crown-styled catheter offers several possible reference configurations in real-time (i.e., without calculation) or near real-time (i.e., based on retrospective calculations): (i) the reference electrode may be the central pole; (ii) the neighboring electrode can serve to create bipolar signals by subtracting one signal from the other; (iii) a received signal from a number of neighboring electrodes (e.g., 4) can be combined to generate a second spatial derivative (Laplacian) signal that is indicative of local normal-to-surface currents; (iv) each external electrode would have a set of nearest internal electrodes as a reference to reduce far field contribution (which may be particularly useful for removing ventricular contribution when mapping the atria); and (v) the electrodes on the central wire (pole) may be used for a reference signal for both the external and internal electrodes of the outer splines. The latter control configuration may be useful if the computer system is to generate separate "external" (full contact) and "internal" (non-contact) maps using the external and internal electrodes sets, respectively. The generation of two maps can enhance reliability of any mapped parameter by probing it simultaneously with two independent systems.

At a block 306, the computer system records multiple signals relative to the reference from all or a subset of the electrodes in the catheter. For the catheter 100, for example, the computer system may collect electrical signals from all external electrodes or from all internal electrodes. In other examples, the computer system may record signals from a subset of either or both of these electrode groupings. The operator can select between various configurations of recordings and reference electrodes with the geometrical information on each of the electrodes from a preset database 214 in the computer system 200 which is based on pre-knowledge of the catheter 100.

At a block 308, the computer system performs initial signal processing on the received electrical signals from the electrodes. Such signal processing may include filtering and transformations that are used to enhance or target certain features of electrical activity. In this way, the electrical signals can be transformed to generate activation maps that optimally correlate with optical mapping based activation maps, which are considered to be the gold standard in cardiac impulse propagation characterization.

The signal processing performed at block 308 may result from transformations developed during a configuration mode of the computer system. In this configuration mode, the computer system executes step-by-step processes to determine a transformation model for use in signal processing. Once configured, that transformation model may be used for the initial signal processing at the block 308. While a configuration mode is described, it will be understood, that such a mode is optional and that mapping and analysis may be achieved from pre-embedded models, from models developing during electrical signal collection, or without transformation signal processing altogether. In any event, an example configuration process includes following.

In the configuration mode, the computer system obtains time series voltage signals in a heart chamber using optical mapping. For a baseline test, the subject's heart chamber may be used, but more generally any reference heart chamber (or historical data thereof) may be used. In place of optical mapping microelectrode recordings may be used, or any other technique to probe the action potentials and accepted in the field of cardiac electrophysiology may be used. The time series data is treated as the baseline data (i.e., gold-standard) that is to be replicated by the electrical recordings in the patients (following a known scaling of frequencies). A separate mapping machine, coupled to the computer system, may provide the optical data. Next, the computer system obtains electrical signals in the vicinity of the gold standard recording sites in the heart chamber, through a mapping catheter as described herein.

To implement the configuration mode, the computer system may compare the electrical signal data against the desired gold standard data. For example, the computer system may cross-correlate the optical signals and the electrical signals together to develop an optimal transformation to match the patients' electrical signals with the gold-standard data. The cross-correlation, for example, may determine an average power spectrum is generated for the gold standard signals during various rhythms a priory (obtained from experiments in animals and scaled to heart rate of the particular patient). The electrical signal is transformed to the frequency domain using a fast Fourier Transformation (FFT) and then multiplied frequency-by-frequency with the optical derived power spectrum, after which the resulting product is transformed back to the time domain.

In place of cross-correlation, other comparison techniques may be used as a part of the configuration mode. The electrical signals may be convolved with previously obtained optical signals collected during fibrillation. In another example, a least square error operator of the sum of the absolute distances $|AE_i - G_i|$ for each time point of the ensemble (i=1 ... n) of electrical signals E(t) and paired gold stand signals G(t) may be minimized by solving for the transformation matrix A, where the matrix A is then used to transform electrical signals in the patients where gold-standard signals are not available. In yet another example, the computer system performs a principal component analysis (PCA) or singular value decomposition (SVD) to analyze and develop a ranking of gold standard signals collected from different modalities. The computer system may then select a subset of high-ranked modalities and average their power spectrum. The computed power spectrum may then be used to perform the electrical signal filtering.

Once the transformations are determined and executed at the block 308, the process 300 then performs a singular value decomposition (SVD) and reconstruction on the set of electrical signals, at block 310. The SVD is used to extract the most important spatio-temporal-spectral characteristics of the patterns of activation within the electrical signal data. Such analysis is useful in analyzing fibrillation and localization of drivers without any pre-assumption on the activation patterns. Numerous SVD techniques will be known for execution at the block 310. Some example SVD techniques are described in Rabinovitch et al., "Singular Value Decomposition of Optically-Mapped Cardiac Rotors and Fibrillatory Activity, Journal of Physics D: Applied Physics, Vol. 48, Issue No. 9, Page 095401 (2015). More broadly, the block 310 is configured to produce data that identifies the most relevant spatio-temporal-spectral components of the received electrical signals using any suitable analysis technique. This reduces the data set to those portions of the data that are most likely to correlate to locations within the cardiac chamber that are the causes of electrical activity abnormalities (e.g., atrial fibrillation) or to those locations within the chamber that are likely candidates for treatment.

At a block 312, the data from block 310 is obtained and a frequency-phase analysis is performed to determine ablation targets. For example, the computer system may analyze patterns of propagation across the catheter electrodes using a phase analysis and independent of signal amplitudes. The computer system will extract phase information on the multi-cyclic electrical activity, such as the phase singularity point that is present at wavebreaks and center of rotors of cardiac electrical activity following Hilbert transformation of the activation time series.

For example, at the block 312, the computer system may segment the electrical signal data from block 310 into to 2 sec to 5 sec long episodes, in which windowing is performed to taper edges to zero. Then, zero padding is performed to a desired time length to accomplish the desired spectral resolution of about 0.2 Hz. Following that, the computer system calculates a continuously sliding, short-period (2 sec to 5 sec long) FFT and Hilbert-based dominant frequency (DF) and activity phase (AP) with a spectral resolution of at least 0.2 Hz. The computer system then performs electrodes-neighborhoods metrics for all electrodes. The DFs are determined based on the power spectrum. The spatial first derivatives of the APs at each moment of time are calculated as well.

The computer system determines two orthogonal AP directionalities (e.g., a circumferential one and a radial one) for all electrodes considering whether they have similar and dissimilar DFs. Circumferential monotonically increasing or decreasing values changes around an electrode that sum up to $\pm 2\pi$ (with a yet to be determined tolerance) over the entire 360 degrees circle values are indicatives of reentry. Monotonic decreases in radial phase in all azimuthal directions away from the electrode are indicative of focal discharge. The computer system identifies those sites having either the circumferential or radial indications as well as those having the highest DFs. These are the sites of potential atrial fibrillation (AF) drivers.

Optionally, the block 312 may determine that additional processing should be performed on the SVD processed data from block 310. Therefore, a block 314 is configured to perform auxiliary time-domain analysis on the received data from block 312 following the SVD and/or frequency-phase processing to enhance ablation targets identification. The block 314 performs an auto-correlation between the voltage time episodes to identify time intervals between sequential local activations. The block 314 may perform a convolution between different signals, e.g., unipolars and bipolars (or multi-polars), to create signals with a reduced far field and reduced directionality artifacts. In addition to the Fourier-based frequency processing in block 312, in block 314, the time domain processing may also perform autocorrelations on each signal to provide another means of calculating the DF for each one of them. The analysis, whether autocorrelation or otherwise, is performed in the time-domain by the block 314, in the present example.

Another optional block 316 performs an adaptive band-pass filtering on the signal data determined at the block 312. At the block 316, for example, the process 300 applies a narrow band pass-filter ($\pm 1$ Hz) around the maximal DF found by the block 312, e.g., taken from all electrodes. Additional band-pass filtering may be implemented bounded by the maximal and minimal DFs of all electrodes.

The additionally processed data from one or both of blocks 314 and 316 are provided to the block 310, which performs another SVD analysis and provides the resulting signal data to the block 312 for further determination of the DF and AP.

At a block 318, the process 300 performs an auxiliary frequency domain analysis designed to enhance ablation targets identification. For example, the computer system may determine, from the Dominant Frequency (DF) calculated by the Fourier transform and in the frequency domain, the relative power at the DF (ratio of power at DF to the power over a broadband, e.g., between 3 Hz and 15 Hz; also called sometimes Regularity Index—RI). The block 318 may also determine an index used to quantify the regularity of the signals (RI) by analyzing the electrical signal data over and entire range of frequencies. The driver of fibrillation is expected to be in many cases at both the highest DF and at the highest RI (except for a possible region in the center of the driver in which the DF should be highest but the RI may be very low). Thus, the computer system determines the product of DF and RI, termed DFRI, as an amplification of the statistical power of the separated factors DF and RI, which then is used by block 318 to identify one or more sites driving the fibrillation. Driver regions of fibrillation are those regions responsible for fibrillation, and may result in fibrillation activity in other regions, where those other regions are called "stand-by" sites.

In some examples, the computer system can produce a digital health report or digital alarm condition. The health report data may be stored for comparison purposes against historical data, for that particular subject or for comparison purposes against a greater sampling size. In other cases, the data may also be displayed to health care professionals for the purposes and establishing a record of possible fibrillation contribution sites.

In the example, the mapping (crown) catheter is bundled with a navigable device, such an endoscope or an ablative catheter, to be manageable by a built-in navigation capabilities. In such examples, at a block 320, the process 300 determines and uses geometrical position of the navigable device inside the chamber. With knowledge of the location and position of the navigable device, the computer system can measure the relative position of the electrodes of the mapping catheter to determine the relative positions of those electrodes, for mapping purposes and for determining ablation sites. In an example, the computer system measures the voltage amplitude of the signals on the multiple electrodes (external electrodes and internal electrodes) that result from a wave generated by an alternating current supplied to a roving electrode associated with the navigable device. This approach is similar to measuring impedance between a roving, navigation catheter and the electrodes of the crown catheter. And while an impedance measurement can be made in some examples, in this example, only a voltage amplitude measurement is made at the electrodes of the mapping catheter. The level of voltage measured at different distances between the crown catheter electrodes and the navigable device then serve to locate (e.g., calculate space coordinates) the navigable device relative to the crown catheter. The advantage of such navigation approach is the simplicity and accuracy relative to existing systems that use an extra-body positioning reference system suffering from non-uniform dielectric properties and motion of the heart, all of which are avoided by having an intra-cardiac multi-points geometrical reference and homogenous dielectric properties (where at least some of the electrodes of the crown catheter are in contact with the cardiac walls).

In an example, the separate, navigable catheter generates at its tip an alternating current with known amplitude and at a frequency of about 0.5-1 kHz (i.e., the quasi static frequency range, but higher than frequencies present in the electrical activity of the heart). The voltage amplitudes in some (>4) electrodes of the crown catheter are then measured (the electrodes are maintained at a uniform potential relative to the ground or a reference point in the heart). The location of the catheter tip is then determined by the relative distance from each electrode, where that distance is inversely and monotonically proportional to the amplitude of the voltage measured in each electrode, without the need to determine the potential difference between the tip and the electrodes.

The techniques herein may be used with an ablation catheter, by specifically determining a position relative to the crown catheter electrodes of the ablation catheter, which is then electrically controlled into position to ablate desired target regions on the chamber surface. The ablation targets are thus identified by the electrical activity mapping from the catheter and corresponding to sources of arrhythmia (block 320). In this way, heart chamber mapping, ablation site identification, and ablation can be achieved without the need to account for the physical dimensions, electrical properties, etc. of the heart and torso. In response, the fibrillation or tachycardia of the subject will be abated with greater efficacy compared with existing devices and approaches.

Figure 4:
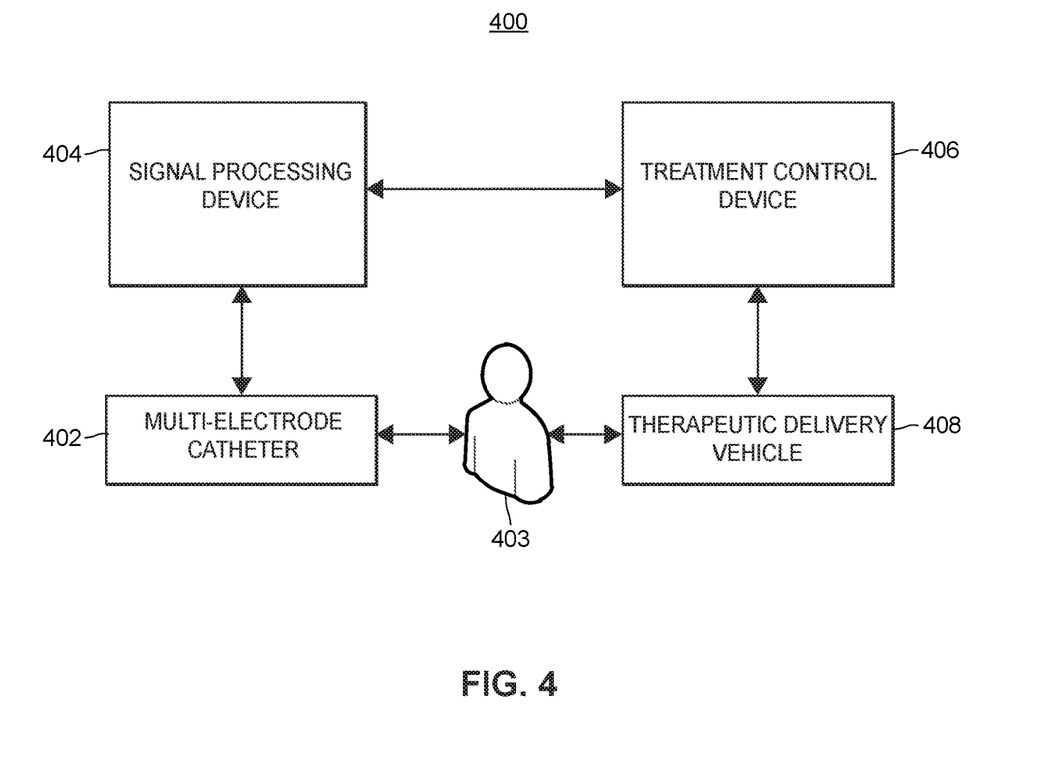
FIG. 4 is a schematic of a therapeutic delivery system for administering a therapeutic treatment to a subject using the apparatus of FIG. 2 in a closed loop manner.

As an example configuration of an electrical mapping and treatment system, FIG. 4 illustrates system 400 in which a therapeutic treatment (e.g., ablation) may be administered in response to mapping and analysis of electrical signals from a multi-electrode catheter. A catheter assembly 402, in accordance with the teachings herein, is inserted into a heart chamber of a subject 403. The catheter assembly 402 collects electrical activity data within the chamber. In some examples, the catheter assembly 402 may include one or more sensors, such as a temperature sensor or an impedance sensor.

A signal-processing device 404, having one or more processors and one or more memories, is coupled to the catheter assembly 402 to receive the electrical signal data and perform signal analysis on the data, in accordance with processes described in FIG. 3. The signal-processing device 404 determines coordinates for applying a treatment, such as source sites for fibrillation that are to be treated with ablation.

The signal-processing device 404 is coupled to a treatment control device 406 that controls a treatment delivery vehicle 408, such as a controllable ablation catheter.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or that are permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or by processor-implemented hardware modules. The performance of certain of the operations may be distributed among the one or more processors, not only residing within a single machine, but also deployed across a number of machines. In some example embodiments, the processor or processors may be located in a single location (e.g., within a hospital, within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a hospital, within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, or refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or an are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A catheter comprising:
a housing providing a sheath to an extendable catheter within the housing; and
the extendable catheter comprising a plurality of splines extendable within the housing when the catheter is in a non-deployed state, the plurality of splines collectively extendable through an opening in the housing and into a deployed state where the plurality of splines erect into a generally three dimensional (3D) shaped catheter head,
wherein, in the deployed state, each of the plurality of splines extends from the opening in the housing to a distal apex point, where each of the plurality of splines is connected at the distal apex point and has a wave-like profile extending the length of each of the plurality of splines, wherein the wave-like profile is characterized by a series of alternating peaks and troughs about an arcuate centerline of a respective spline, and
wherein for each of the plurality of splines, in the deployed state, the splines extend independently from each other such that at least some of the respective alternating peaks and troughs of the wave-like profile of each of the plurality of splines lie in respective planes that intersect at a longitudinal axis of the catheter, and
wherein each of the plurality of splines comprises non-conducting regions, and
wherein each of the plurality of splines further comprises electrodes distributed across the respective spline to collect electrical activity signal data across the respective spline, such that in the deployed state the catheter comprises the electrodes positioned for collecting electrical activity signal data over a volumetric space within a target chamber, and
wherein at least one of the electrodes is positioned on a peak and at least one of the electrodes is positioned on a trough.

2. The catheter of claim 1, wherein the alternating peaks and troughs have fixed or varying amplitudes, fixed or varying curvatures, and/or fixed or varying shapes.

3. The catheter of claim 2, wherein the electrodes on each of the plurality of splines are positioned on the peaks and/or the troughs.

4. The catheter of claim 2, wherein for each of the plurality of splines a first set of the electrodes are positioned on the peaks and a second set of the electrodes are positioned on the troughs.

5. The catheter of claim 2, wherein for each of the plurality of splines a first set of the electrodes are positioned on an outer surface of the respective spline to provide an externally directed sensing region and a second set of the electrodes are positioned on an inner surface of the respective spline to provide an internally directed sensing region.

6. The catheter of claim 1, wherein the electrodes are embedded in the plurality of splines.

7. The catheter of claim 1, wherein the electrodes are fabricated into the plurality of splines.

8. The catheter of claim 1, further comprising a central spline extending along an axis of the catheter head in the deployed position.

9. The catheter of claim 8, wherein the catheter is steerable by controlled movement of the central spline to deflect the catheter head into different directions.

10. An electrical activity mapping system comprising:
a catheter comprising:
a housing providing a sheath to an extendable catheter within the housing; and
the extendable catheter comprising a plurality of splines extendable within the housing when the catheter is in a non-deployed state, the plurality of splines collectively extendable through an opening in the housing and into a deployed state where the plurality of splines erect into a generally three dimensional (3D) shaped catheter head,
wherein, in the deployed state, each of the plurality of splines extends from the opening in the housing to a distal apex point, where each of the plurality of splines is connected at the distal apex point and has a wave-like profile extending the length of the spline, wherein the wave-like profile is characterized by a series of alternating peaks and troughs about an arcuate centerline of a respective spline, and
wherein for each of the plurality of splines, in the deployed state, the plurality of splines extend independently from each other such that at least some of the respective alternating peaks and troughs of the wave-like profile of each of the plurality of splines lie in respective planes that intersect a longitudinal axis of the catheter, and
wherein each of the plurality of splines comprises non-conducting regions, and
wherein each of the plurality of splines further comprises electrodes distributed across the respective spline to collect electrical activity signal data across the spline, such that in the deployed state the catheter comprises the electrodes positioned for collecting electrical activity signal data over a volumetric space within a target chamber, and
wherein at least one of the electrodes is positioned on a peak and at least one of the electrodes is positioned on a trough;
one or more processors coupled to the electrodes of the catheter; and
one or more non-transitory computer readable memories coupled to the one or more processors, wherein the one or more memories include computer-executable instructions stored therein that, when executed by the one or more processors, cause the one or more processors to:
receive electrical signal data from at least some of the electrodes of the catheter;
map electrical activity within the target chamber from the electrical signal data; and
identify, from the mapping, (i) potential sources of fibrillation and/or arrhythmia within the target chamber and/or (ii) an alarm condition indicating a presence or onset of fibrillation and/or arrhythmia.

11. The electrical activity mapping system of claim 10, wherein the one or more memories include computer-executable instructions stored therein that, when executed by the one or more processors, cause the one or more processors to: produce a digital health report for the target chamber or a digital alarm condition indicating the presence or onset of fibrillation and/or arrhythmia; and communicate that digital health report or the digital alarm condition through a visual display.

12. The electrical activity mapping system of claim 10, wherein the one or more memories include computer-executable instructions stored therein that, when executed by the one or more processors, cause the one or more processors to map electrical activity within the target chamber by causing the one or more processors to: perform a singular value decomposition processing on the received electrical signal data to extract spatio-temporal characteristics and/or patterns in the received electrical signal data; and extract phase information including at least one phase singularity point data for the target chamber.

13. The electrical activity mapping system of claim 12, wherein the one or more memories include computer-executable instructions stored therein that, when executed by the one or more processors, cause the one or more processors to map electrical activity within the chamber by causing the one or more processors to: analyze the received electrical signal data in the frequency domain to identify sources of dominant frequency; analyze the received electrical signal data in the phase domain to identify sources of activity phase; and in response, determine the at least one phase singularity point data.

14. The electrical activity mapping system of claim 12, wherein the one or more memories include computer-executable instructions stored therein that, when executed by the one or more processors, cause the one or more processors to map electrical activity within the chamber by causing the one or more processors to: analyze the received electrical signal data in the phase domain to determine orthogonal activity phase directionalities for each of the electrodes of the catheter.

15. The electrical activity mapping system of claim 10, wherein the one or more memories include computer-executable instructions stored therein that, when executed by the one or more processors, cause the one or more processors to: in response to identifying, from the mapping, the potential sources of fibrillation and/or arrhythmia within the target chamber, determine targeted treatment instructions and communicate the targeted treatment instructions to a treatment device.

16. The electrical activity mapping system of claim 15, wherein the treatment device is an ablation catheter deployed within the target chamber.

17. The electrical activity mapping system of claim 10, further comprising a navigation device, and wherein the one or more memories include computer-executable instructions stored therein that, when executed by the one or more processors, cause the one or more processors to provide navigation data for adjusting the position of the catheter relative to the navigation device.

18. The electrical activity mapping system of claim 10, wherein the one or more memories include computer-executable instructions stored therein that, when executed by the one or more processors, cause the one or more processors to measure voltage signals from at least some of the electrodes on at least some of the plurality of splines, where the amplitudes of the voltage signals indicate distances between the navigation device and the at least some of the plurality of splines.

19. The electrical activity mapping system of claim 10, wherein the one or more memories include computer-executable instructions stored therein that, when executed by the one or more processors, cause the one or more processors to provide reference signal data for the catheter, wherein the reference signal is provided on (i) a central pole of the catheter extending along a central axis of the plurality of splines, or (ii) on one or more of the electrodes of the plurality of splines.

\* \* \* \* \*